(12) United States Patent
Wilson et al.

(10) Patent No.: US 10,602,913 B2
(45) Date of Patent: Mar. 31, 2020

(54) OPTICAL DOCKING SYSTEM WITH INDUCTIVE POWERING FOR CAPSULE CAMERA

(71) Applicant: CapsoVision, Inc., Saratoga, CA (US)

(72) Inventors: Gordon C. Wilson, San Francisco, CA (US); Jiafu Luo, Irvine, CA (US); Kang-Huai Wang, Saratoga, CA (US); Chung-Ta Lee, Sunnyvale, CA (US)

(73) Assignee: CAPSOVISION INC., Saratoga, CA (US)

( * ) Notice: Subject to any disclaimer, the term of this patent is extended or adjusted under 35 U.S.C. 154(b) by 0 days.

(21) Appl. No.: 16/388,261

(22) Filed: Apr. 18, 2019

(65) Prior Publication Data

US 2019/0239721 A1 Aug. 8, 2019

Related U.S. Application Data

(62) Division of application No. 14/401,521, filed as application No. PCT/US2013/039317 on May 2, 2013, now abandoned.
(Continued)

(51) Int. Cl.
*A61B 1/00* (2006.01)
*A61B 1/04* (2006.01)
*A61B 5/07* (2006.01)

(52) U.S. Cl.
CPC ...... *A61B 1/00013* (2013.01); *A61B 1/00006* (2013.01); *A61B 1/00016* (2013.01);
(Continued)

(58) Field of Classification Search
CPC ............ A61B 1/00013; A61B 1/00006; A61B 1/00016; A61B 1/0002; A61B 1/00022;
(Continued)

(56) References Cited

U.S. PATENT DOCUMENTS 7,983,458 B2 7/2011 Wang et al.
2008/0257768 A1* 10/2008 Uchiyama .......... A61B 1/00144
206/350

(Continued)

FOREIGN PATENT DOCUMENTS

JP 2005102851 A 4/2005
JP 2011-39111 A 9/2011
WO WO-2011074344 A1 * 6/2011 ......... A61B 1/00036

*Primary Examiner* — Ryan N Henderson
*Assistant Examiner* — Pamela F Wu
(74) *Attorney, Agent, or Firm* — Edward C. Kwok; VLP Law Group, LLP

(57) ABSTRACT

A capsule endoscopic system is disclosed, where the system comprises a capsule device and a docking device. The capsule device comprises a battery, a secondary coil, an optical transmitter all enclosed in a capsule housing. The docking device comprises a primary coil to generate an alternating magnetic field, a primary core and optical receiver to receive an optical signal. The alternating magnetic field is coupled to the secondary coil to supply power to the capsule device when the capsule device is at a docked position in the docking device. The primary core is arranged to concentrate the alternating magnetic field on the secondary coil when the capsule device is at the docked position. Furthermore, the capsule endoscopic system is arranged so that an optical path is formed between the optical transmitter and the optical receiver when the capsule device is at the docked position.

13 Claims, 14 Drawing Sheets

Related U.S. Application Data

(60) Provisional application No. 61/649,238, filed on May 19, 2012.

(52) U.S. Cl.
CPC ...... *A61B 1/00029* (2013.01); *A61B 1/00032* (2013.01); *A61B 1/00034* (2013.01); *A61B 1/00055* (2013.01); *A61B 1/00144* (2013.01); *A61B 1/00158* (2013.01); *A61B 1/041* (2013.01); *A61B 5/073* (2013.01); *A61B 2560/0204* (2013.01); *A61B 2560/0456* (2013.01)

(58) Field of Classification Search
CPC ............ A61B 1/00025; A61B 1/00027; A61B 1/00029; A61B 1/00032; A61B 1/00034; A61B 1/00036; A61B 1/00112; A61B 1/04; A61B 1/041; A61B 1/00055; A61B 1/00144; A61B 1/00158; A61B 5/073; A61B 2560/0204; A61B 2560/0456
USPC ...................................................... 600/109
See application file for complete search history.

(56) References Cited

U.S. PATENT DOCUMENTS

| | | | | |
|---|---|---|---|---|
| 2008/0260319 | A1* | 10/2008 | Taira | G02F 1/011 385/1 |
| 2009/0306474 | A1* | 12/2009 | Wilson | A61B 1/041 600/109 |
| 2012/0007973 | A1* | 1/2012 | Tsutsumi | A61B 1/00016 348/65 |
| 2012/0232344 | A1* | 9/2012 | Sato | A61B 1/00036 600/109 |

* cited by examiner

OPTICAL DOCKING SYSTEM WITH INDUCTIVE POWERING FOR CAPSULE CAMERA

CROSS REFERENCE TO RELATED APPLICATIONS

The present invention is a division of and claims priority to U.S. Non-Provisional application Ser. No. 14/401,521, filed on Nov. 16, 2014, which is a 371 of PCT/US2013/039317, filed on May 2, 2013, which claims priority to U.S. Provisional Patent Application, No. 61/649,238, filed on May 19, 2012. The U.S. Provisional patent application, PCT patent application, and U.S. Provisional patent application are hereby incorporated by reference in their entireties.

FIELD OF THE INVENTION

The present invention relates to diagnostic imaging inside the human body. In particular, the present invention relates to an optical docking system for supplying power inductively to and retrieving data from a capsule camera.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. Alternatively, the endoscope might record an image electronically at the distal end, for example using a CCD or CMOS array, and transfer the image data as an electrical signal to the proximal end through a cable. Because of the difficulty traversing a convoluted passage, endoscopes cannot easily reach the majority of the small intestine and special techniques and precautions, that add cost, are required to reach its entirety. The cecum and ascending colon also require significant effort and skill to reach with an endoscope. An alternative in vivo image sensor that addresses many of these problems is a capsule endoscope. A camera is housed in a swallowable capsule, along with a radio transmitter for transmitting data, primarily comprising images recorded by the digital camera, to a base-station receiver or transceiver and data recorder outside the body. Another autonomous capsule camera system with on-board data storage was disclosed in the U.S. patent application Ser. No. 11/533,304, filed on Sep. 19, 2006.

For the above in vivo devices, a large amount of image data is collected traversing through a lumen in the human body such as the gastrointestinal (GI) tract. The images captured, along with other information, are stored in the on-board archival memory inside the capsule camera. The archival memory may come in various forms of non-volatile memories. After the capsule camera exits from the anus, it is retrieved to recover the data stored on-board. In a conventional approach, it would require a fairly expensive data access system that includes opening the capsule and docking to it. Because of the requirement to open the capsule and align contact pins to pads in the capsule, some degree of mechanical complexity is inevitable. Therefore, such tasks usually are performed by specially trained persons. It is desirable to develop a new system that allows data retrieval from the capsule camera without opening the sealed enclosure. Furthermore, it is desired that the new system can operated be easily and quickly so that data retrieval from the capsule camera can be performed in any typical medical service environment.

BRIEF SUMMARY OF THE INVENTION

A capsule endoscopic system is disclosed, where the system comprises a capsule device and a docking device. The capsule device comprises a battery, a secondary coil, an optical transmitter and a capsule housing adapted to be swallowable and to enclose the battery, the secondary coil and the optical transmitter in a sealed environment. The docking device comprises a primary coil to generate an alternating magnetic field, a primary core and optical receiver to receive an optical signal. The alternating magnetic field is coupled to the secondary coil to supply power to the capsule device when the capsule device is at a docked position in the docking device. The primary core is arranged to concentrate the alternating magnetic field on the secondary coil when the capsule device is at the docked position. Furthermore, the capsule endoscopic system is arranged so that an optical path is formed between the optical transmitter and the optical receiver when the capsule device is at the docked position, and where the optical path includes a line passing through the optical transmitter and the secondary coil.

In one embodiment, the line passes through a longitudinal axis of the capsule device. Furthermore, the capsule housing contacts a receptacle inside the docking device, and the receptacle and the capsule housing are shaped such that the longitudinal axis of the capsule device is stationary as the capsule device is rotated in the docked position. The post may further have a bore through the axis of the post, and the light from the optical transmitter in the capsule device passes through the bore to the optical receiver in the docking device. The docking device may further comprise a receptacle to hold the capsule device and the receptacle comprises a tapered inner surface to mate with a curved surface of a first longitudinal end of the capsule device, and wherein the line passes through to the first longitudinal end of the capsule device. At least a portion of the first longitudinal end of the capsule device is transparent to allow the light from the optical transmitter to pass through.

In one embodiment, the capsule device further comprises an archival memory to store data captured when the capsule device traveled through a human GI (gastrointestinal) tract, and the archival memory is enclosed in the capsule housing. The capsule device further comprises a control circuit coupled to the archival memory and the optical transmitter, where the control circuit is configured to read stored data from the archival memory and to provide the stored data to the optical transmitter.

In one embodiment, the optical transmitter generates modulated light. Furthermore, the docking device may comprise a lens of positive refractive power to reduce divergence of the modulated light.

In one embodiment, the docking device further comprises a receptacle to hold the capsule device and the receptacle comprises a tapered inner surface to mate with a curved surface of a first longitudinal end of the capsule device, where the line passes through to the first longitudinal end of the capsule device. Furthermore, at least a portion of the first longitudinal end of the capsule device is transparent to allow light from the optical transmitter to pass through.

DETAILED DESCRIPTION OF THE INVENTION

Figure 1:
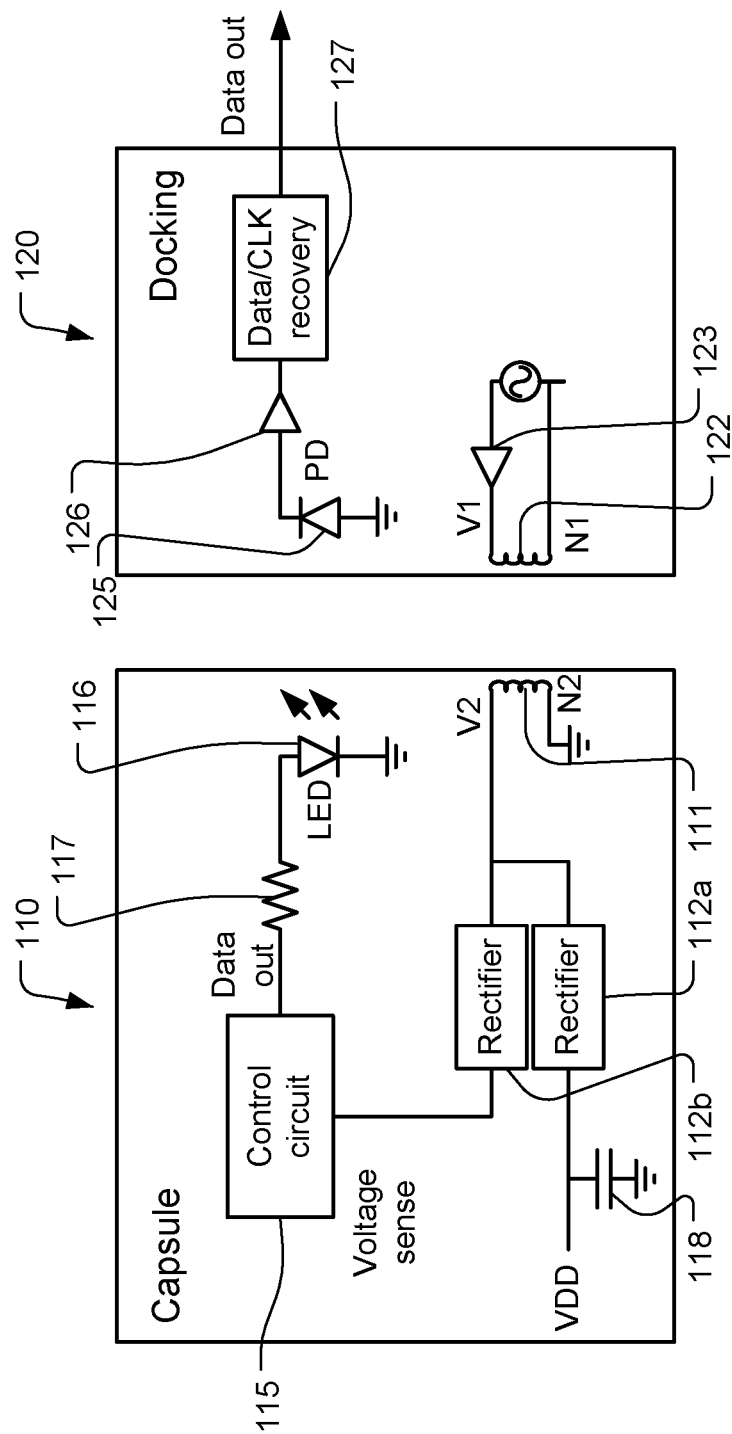
FIG. 1 illustrates an example of system architecture of an optical wireless docking system according to the present invention.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

In order to overcome the shortcoming in a conventional docking system, an optical wireless docking system according to the present invention is disclosed herein. A wireless docking system is attractive because the capsule need not be opened or precisely aligned. After the capsule camera exits from the anus, the batteries inside are likely depleted or nearly depleted. Therefore, power must be supplied from outside the capsule, by magnetic induction for example. Also, data has to be transmitted wirelessly, such as by an optical or radio means.

In one embodiment according to the present invention, the docking system utilizes inductive powering and optical transmission. Nevertheless, radio transmission may also be used to practice the present invention. Any optical source requiring very little space to fit into the capsule may be considered. The optical source should be able to support fast data transmission. The amount of data stored in a capsule camera may be as much as 500 Mbytes and the data size will continue to grow along with the trend of high-resolution demand. If 1 Mbps (million bits per second) transmission speed is supported, it may take around 100 minutes to read out 500 Mbytes data if overhead in data transmission protocol is taken into account. Therefore, it is preferably to select an optical source that can support higher data rate. As one example, the optical source can be a directly modulated LED or Vertical-Cavity Surface-Emitting Laser diode (VCSEL) with a target bit rate of 10 Mbps.

Exemplary system architecture is shown in FIG. 1, where LED 116 is used as a light source and a Photo Diode (PD) is used as the receiver. Control circuit 115 is shown inside capsule camera 110. Control circuit 115 will read data stored in the archival memory (not shown) and process the retrieved data so that the data can be properly transmitted by light source 116. Light emitted from light source 116 will travel through the transparent window (not explicitly shown) of the capsule camera. The light from light source 116 will be received by a light receiving device such as photo diode 125 at docking system 120. The received signal will be properly amplified by amplifier 126. The amplified signal is then processed by receiver circuit 127 where data and clock will be recovered. The data recovered can be stored on a media such as a flash drive or computer hard disk drive. Alternatively, the data recovered may be provided to a workstation or a display station for further processing or viewing.

The output buffer from control circuit 115 will provide needed power for light source 116. For example, 2 mA current may be provided, which should be adequate to drive either an LED or VCSEL. The LED wavelength may be in the near Infrared (NIR), for example at 830 nm. Other LED wavelengths may also be used to practice the present invention. With a 3V drive voltage, the correct drive current is produced with series resistance 117. A bit rate of 10 Mbps or more can be achieved.

The receiver consists of photodiode 125, trans-impedance amplifier 126, and data/clock recovery module 127. This module could be implemented using a limiting amplifier and a PLL. However, this functionality could be performed digitally by sampling the waveform and using DSP to recover data and clock. The use of a UART might obviate the need for clock recovery. The interface protocol may be used for the intended operation around 10 Mbps frequency range. Other standard digital data interfaces may also be used. In FIG. 1, optical link is shown as a wireless link between the capsule device and the docking device, a radio frequency (RF) link may also be used as the wireless link.

Inductive coupling relies on the mutual inductance of a primary coil outside the capsule and a secondary coil inside the capsule. The primary coil is driven by a sinusoidal voltage, and the secondary signal is rectified to produce a DC voltage. Exemplary system architecture is shown in FIG. 1. The system comprises capsule camera 110 and docking system 120. The inductive power is supplied from docking system 120 to capsule camera 110 through coupling coils 122 and 111. Coil 122 at the docking system side is referred to as primary side and coil 111 on the capsule camera side is referred to the secondary side. At the primary side, signal source 121 provides the driving signal to primary coil 122. While a sinusoidal driving signal is shown, other alternating signals such as square wave or triangular wave may also be used. The driving signal from signal source 121 may be amplified by amplifier 123. Various other known means of producing an alternating current may be utilized to drive the primary. The voltage across primary coil 122 is named primary voltage V1 and the voltage across secondary coil 111 is named secondary voltage V2. It is well known in the art that the induced alternating voltage at the secondary side can be converted into a DC voltage to be used by the circuits inside the capsule camera. Rectifiers are often used for converting AC power to DC power. Two rectifiers 112a and 112b are shown in FIG. 1 to provide different DC outputs as required by the capsule camera. Furthermore, the circuits in the capsule device can be configured to charge rechargeable batteries inside the capsule device when the capsule device is docked in the docking device. For example, battery 118 may be a rechargeable battery and can be charged by the voltage output from rectifier 112a. Depending on the capsule camera design, it may require more or fewer voltage outputs. The rectifiers may also be integrated into a package or a module. The rectifier may be followed by a simple regulator, such as a Zenor-diode circuit or other voltage control circuits, to allow larger variability and stability in secondary voltage. Additionally, the rectifier may include voltage multiplication with a Greinacher or Cockcroft-Walton circuit. The components are selected to minimize the volume in order to fit into the limited space available inside the capsule camera. A voltage multiplier allows a smaller and lighter secondary coil to be used but requires additional diodes and capacitors.

The ratio of the secondary to primary voltage is:

$$\frac{V_2}{V_1} = \beta \frac{N_2}{N_1}, \quad (1)$$

where $N_2$ is the number of secondary coil turns, $N_1$ is the number of primary coil turns. The coupling coefficient is the ratio of the coil fluxes:

$$\beta = \frac{\phi_2}{\phi_1}. \quad (2)$$

The flux through a coil is given by integration of the flux density through a surface defined by the coil perimeter $$\phi_i = \int_S B_i \cdot dS_i. \quad (3)$$

The coupling coefficient $\beta$ can be increased by making the secondary coil area larger and by designing pole pieces for the primary and/or secondary that concentrate the magnetic flux. For sinusoidal modulation of the primary at frequency f, the flux amplitude in the primary and secondary is given by $$\phi_i = \frac{V_i}{\sqrt{2}\pi f N_i} \quad (4)$$

Figure 2A:
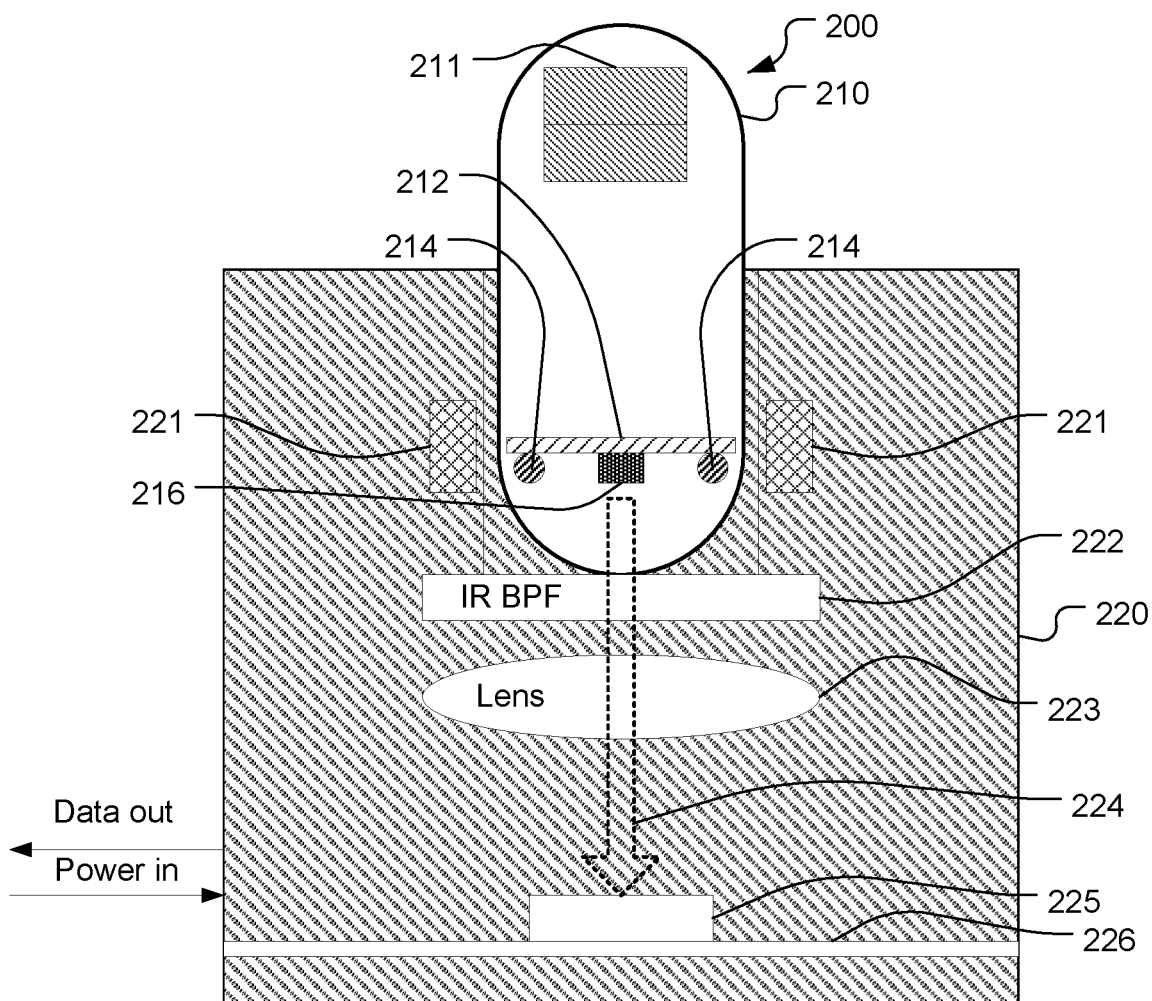
FIGS. 2A-B illustrate an exemplary optical wireless docking system according to the present invention, where the system is configured with longitudinal-field geometry.
Figure 2B:
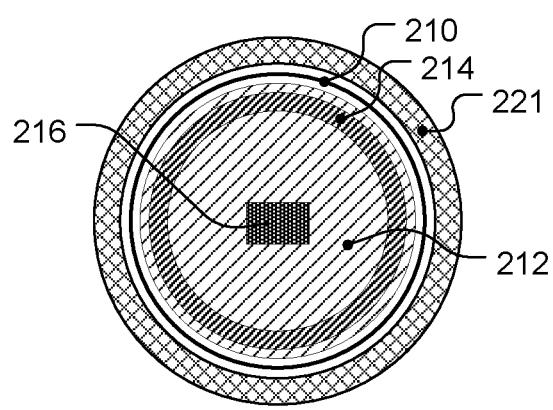

As mentioned before, the secondary coil is located inside the capsule camera. In order to properly couple the electromagnetic field from the primary coil to the secondary coil, the two coils have to be correctly positioned and aligned. On the other hand, in order to read out data from the capsule camera optically, light passage has to be provided between the light source and the light detector. Accordingly, one exemplary system configuration to provide light passage as well as magnetic field coupling is shown in cross section in FIGS. 2A and 2B, where FIG. 2B represents a bottom view of the capsule camera. The type of arrangement is called longitudinal-field geometry.

Primary coil 221 wraps around capsule housing 210 of capsule 200. Secondary coil 214 is on the perimeter of bottom PCB 212 in the capsule. Primary coil 221 and secondary coil 214 should be centered on the same plane. Secondary coil 221 can also be implemented as a printed circuit as a spiral on multiple layers of PCB 212, although the practical pitch of the traces limits the number of turns. Alternatively, a coil can be produced with thin-gauge insulated wires held in shape with shellac and mounted to the PCB as a through-hole or surface mount component.

Light source 216 (LED or VCSEL) sits on the center of the board facing down. Batteries 211 are located at the other end of the capsule camera so that the batteries will not block light passage 224 from the light source to the light receiver. Lens 223 may be used to focus the light onto light receiver 225 such as a photodiode. Optional Band Pass Filter (BPF) 222 for the light can be installed in light passage 224 between light source 216 and light receiver 225. The components including the primary coil 221, the light BPF 222, the lens 223, the light receiver 225 and associated Printed Circuit Board 226 are housed in the docking system 220. The arrangement is symmetrical so that the rotational orientation of the capsule is not significant to the inductive coupling or the received optical power. A disadvantage is that eddy currents will be induced in the traces and power planes on PCB 212 itself. These currents can cause heating and also produce noise in the circuit. In the worst case, where a circuit trace forms a loop around the PCB, the induced voltage in the trace is $V_2/N_2$. Increasing the number of turns will decrease the noise but increase the volume occupied by the secondary coil. The noise can also be limited by minimizing the loop area of traces.

Figure 3:
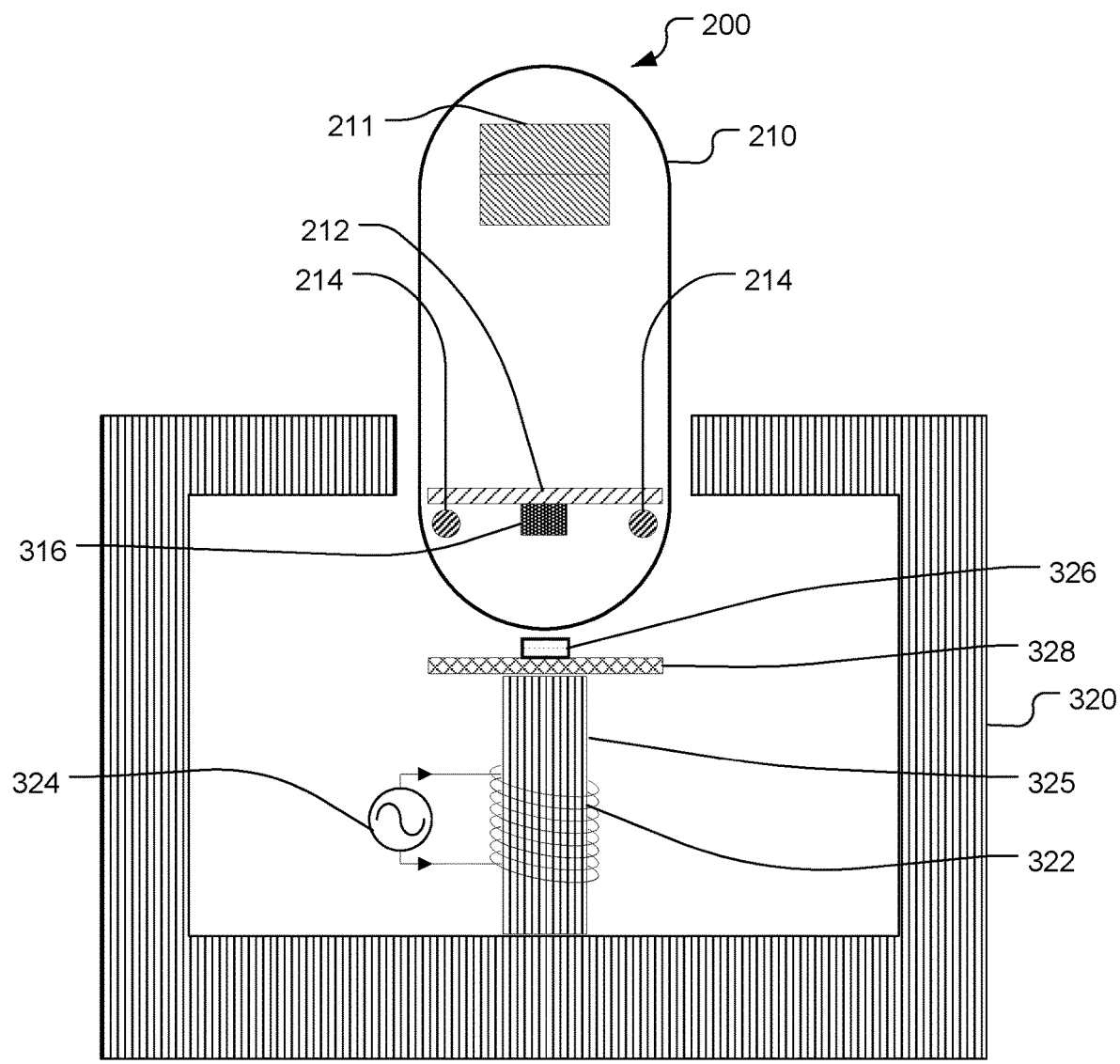
FIG. 3 illustrates an exemplary optical wireless docking system according to the present invention, where the system is configured with alternative longitudinal-field geometry.

FIG. 3 illustrates another primary coil arrangement where ferrite core 320 for the primary coil on the primary side can reduce the magnetic flux reaching the batteries. The ferrite core 320 is also referred to as a primary core in this disclosure. The primary core may have a shell structure to enclose the primary coil. The shell has an opening to allow the capsule device to be docked through the opening. The primary core may be a ferrimagnetic material or may be a ferromagnetic material such as steel. A ferrite has the advantage of low electrical conductivity and, as a result, low eddy current loss. Coin-cell silver oxide or lithium batteries have high energy density and a round package that fits well in a capsule, but these generally have steel cases that could be inductively heated, creating the potential for battery bursting. The core also will reduce the field emitted by the system, which might be an issue for electromagnetic compatibility (EMC) requirement compliance. Photodiode 326, mounted on PCB 328, sits above post piece 325. Primary coil 322 is wrapped around post piece 325. Signal source 324 provides driving signal to primary coil 322. This design has no lens, but uses VCSEL 316, which has an output beam with much lower divergence than an LED.

Figure 4:
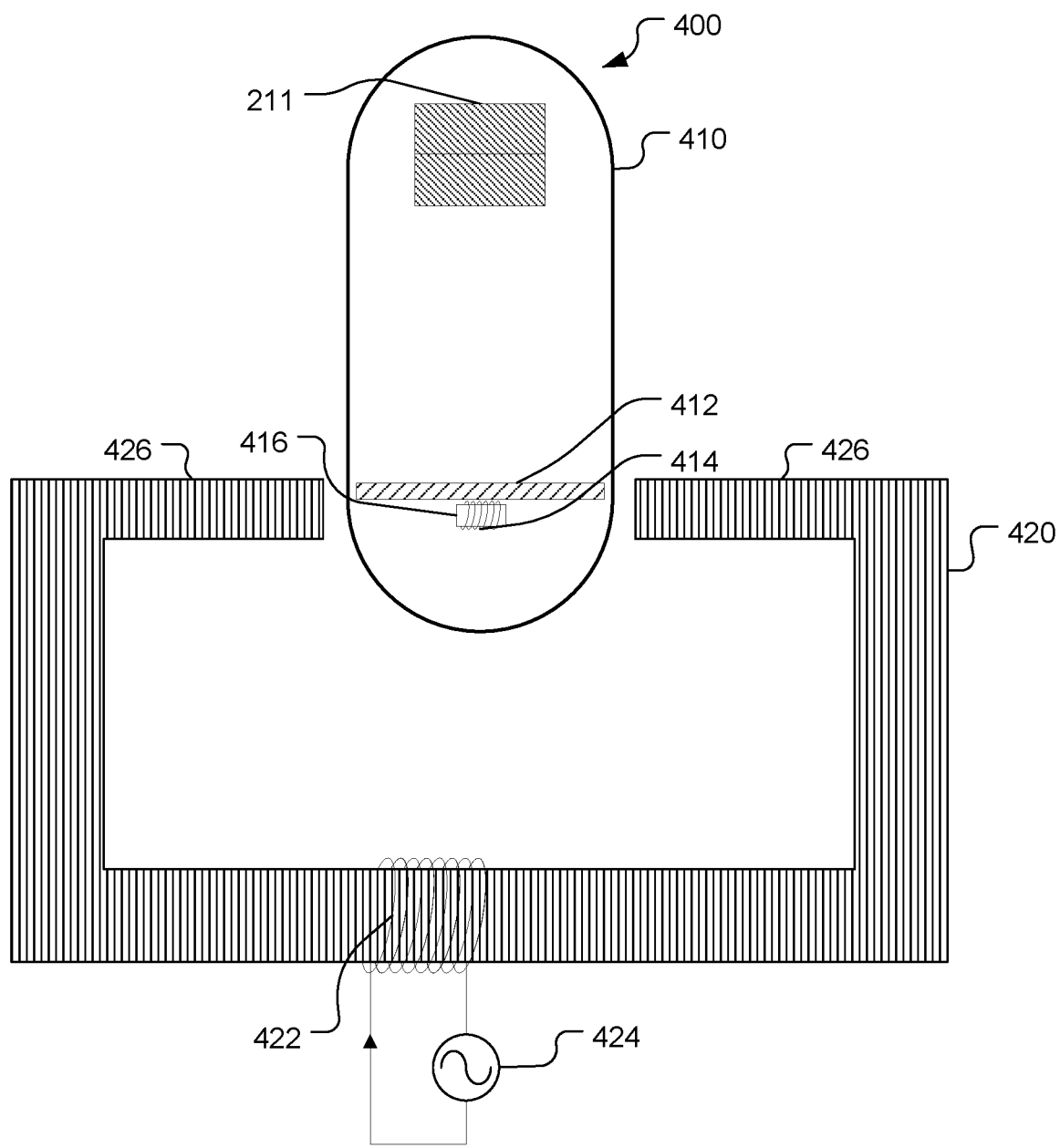
FIG. 4 illustrates an exemplary optical wireless docking system according to the present invention, where the system is configured with lateral-field geometry.

The problem of spurious eddy currents can be reduced by orienting the field horizontally to PCB and batteries as shown in FIG. 4. The arrangement between the primary coil and secondary coil is named lateral-field geometry. Small coil 414 wrapped around ferrite 416 is placed on PCB 412 aligned to the post pieces 426. Capsule 400 with housing 410 must be oriented to post pieces 426. β is reduced relative to the geometry of FIG. 2A because of the small area of secondary coil 414. On the other hand, ferrite core 416 will concentrate the field lines within secondary coil 414 to some degree. This effect is maximized if the gap between the post pieces is minimized and the length of the ferrite 416 is maximized. However, the length is limited by the available space in the capsule. Primary coil 422 is wrapped around primary core 420 and is driven by driving signal 424. While a C-shaped primary core is used, a toroidal-shaped structure or similar can also be used.

Figure 5:
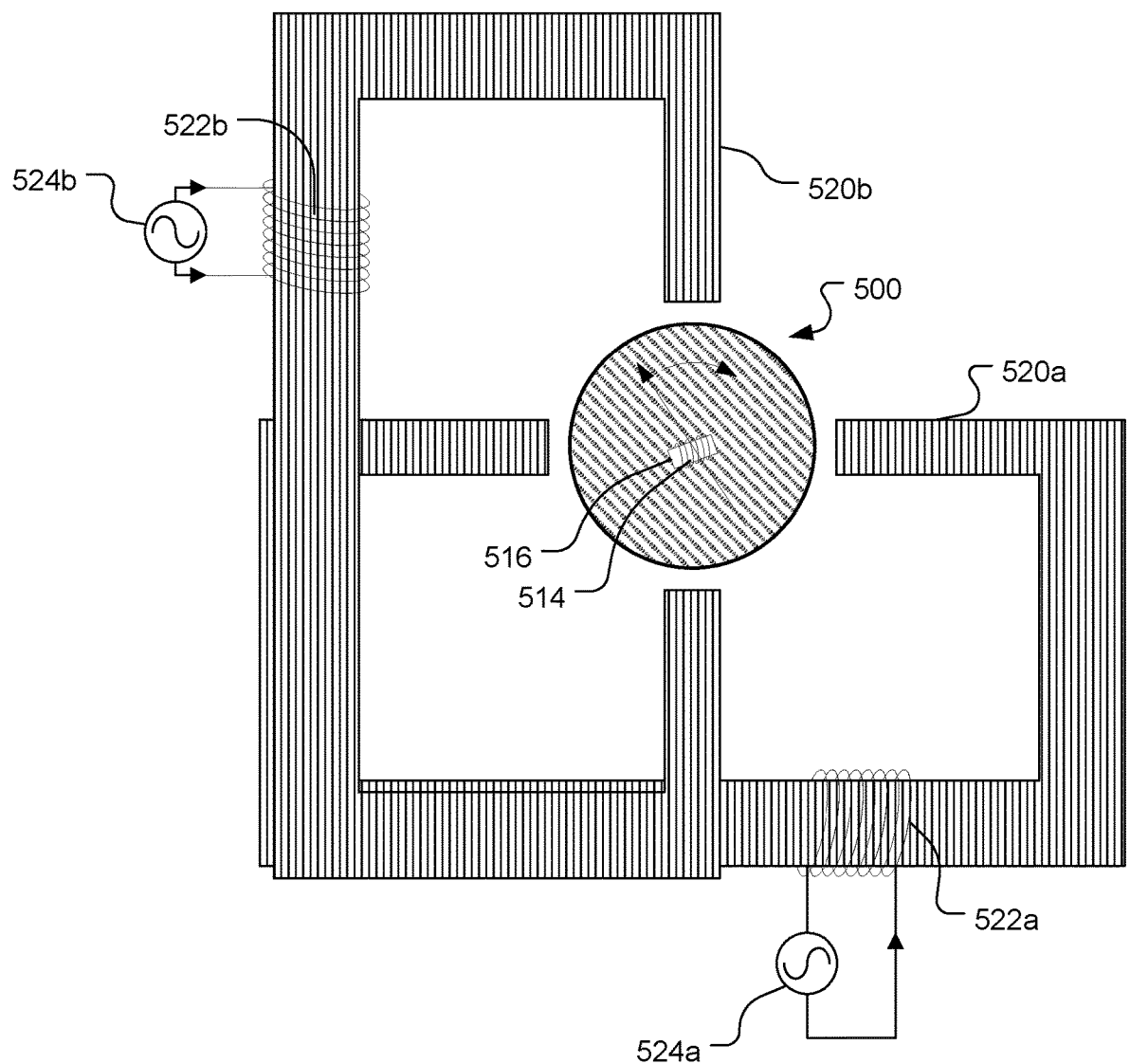
FIG. 5 illustrates an exemplary optical wireless docking system according to the present invention, where the system is configured with lateral-field geometry using two sets of primary ferrites with poles positioned orthogonally.

To avoid the requirement of capsule alignment, a second set of pole pieces can be placed orthogonal to the first and driven in quadrature as shown in FIG. 5, where a top view is presented. The pole pieces of first primary ferrite 520a are configured to be orthogonal to the pole pieces of second primary ferrite 520b. First primary coil 522a is driven by first driving signal 524a and second primary coil 522b is driven by second driving signal 524b. Driving signals 524a and 524b have to be quadrature. For example, the pair of signals $I_0 \cos(2\pi ft)$ and $I_0 \cos(2\pi ft + \pi/2)$ can be used to drive signal sources 524a and 524b. Capsule 500 is shown at the center of the sets of poles. Secondary coil 514 is wrapped around ferrite core 516. The orientation of the secondary coil is shown at a slant angle from the orientations of the two sets of poles. The magnetic field will rotate and the flux through the coil will vary approximately sinusoidally independent of capsule orientation. The flux amplitude will have some dependence on orientation if the secondary ferrite is not rotationally symmetrical, however.

The secondary coil may be an off-the-shelf inductor, as long as it is not shielded. Surface-mount inductors that comprise a ferrite with a fine wire wrapping it would be a convenient and low-cost solution. For example, two chip inductors from CoilCraft that could be used are:

| | | |
|---|---|---|
| 0805LS-273XJLB | 27 µH | 15 mg |
| 0603LS-223XJLB | 22 µH | 5 mg |

The 0805LS-273 has a coil cross section of $A_2 \approx 1.5$ mm$^2$. Assume the primary pole pieces have an area of $A_1 \approx 32$ mm$^2$. The magnetic flux density in the secondary will be less than that in the primary due to field fringing, although the ferrite in the secondary will concentrate the field to some extent. As a rough estimate, assume the flux density is reduced by 10X. The coupling is thus $$\beta \approx \frac{A_1}{10 A_2} \approx 0.005$$

and $V_1/V_2 \approx 200 N_1/N_2$.

A disadvantage of low coupling is worse load regulation. The inductor could be placed at the periphery of capsule close to a pole piece to further increase coupling. However, an alignment of the capsule would be required.

Figure 6:
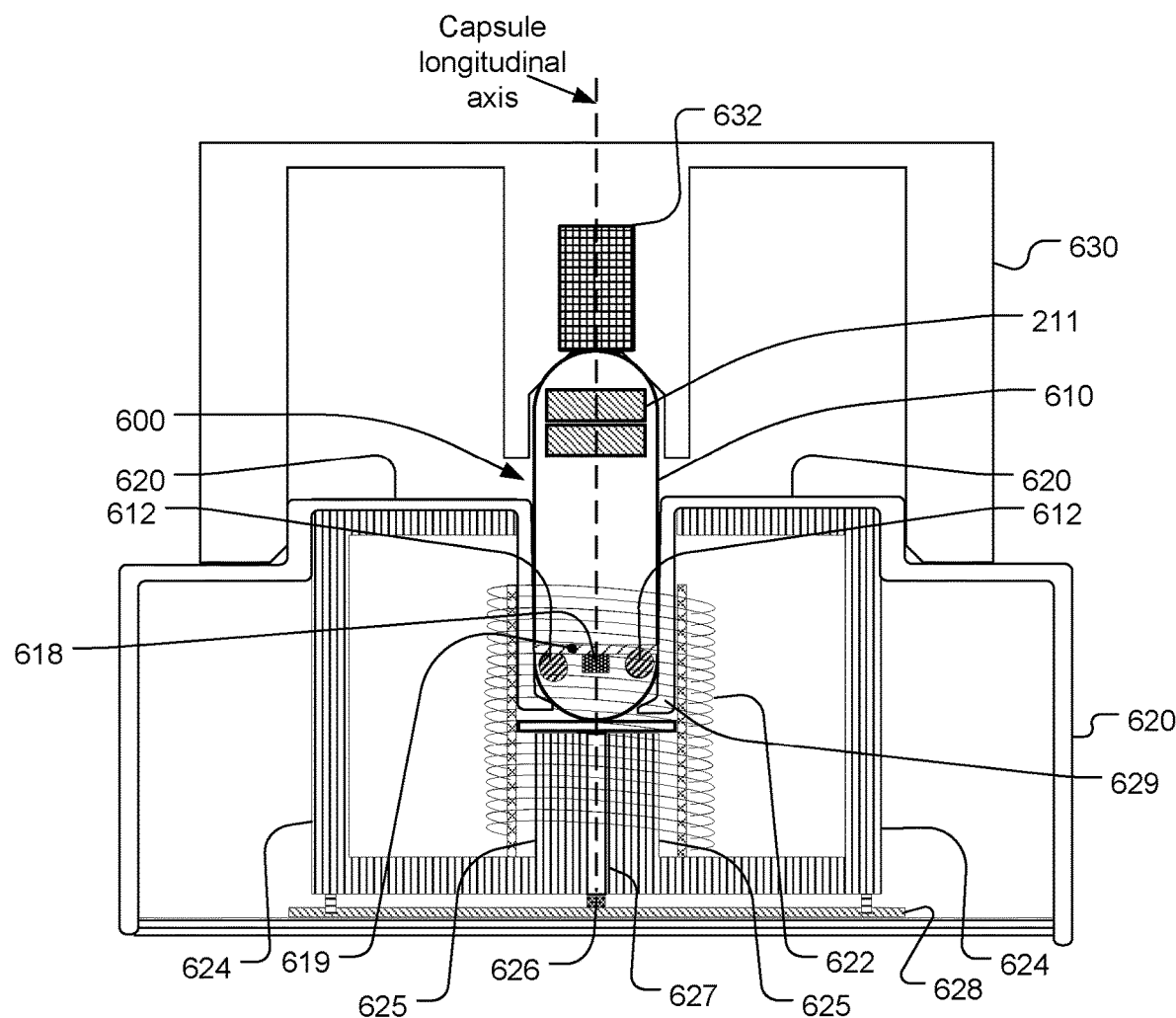
FIG. 6 illustrates a cross-section view of an exemplary optical wireless docking system according to the present invention, where the system is configured with longitudinal-field geometry.

The capsule can be inserted into an opening in the system housing. At the bottom of the hole is a window, where a band pass filter at the LED wavelength can be placed. A lens may be used to focus the emitted light onto the photodiode. FIG. 6 illustrates an exemplary optical wireless docking system according to the present invention. The components for the docking device side can be placed inside the docking device housing. The exemplary docking system in FIG. 6 consists of base part 620 and holder part or cover part 630. Holder/cover part 630 can be pulled open or separated from the base part to insert or remove capsule 600. Secondary coil 612 inside the capsule and primary coil 622 are configured longitudinally. Part of the primary coil is wrapped around center post 625 of primary ferrite 624 (or primary core).

The primary ferrite has a shell-shaped structure to provide passage 627 between light source 618 inside capsule 600 and light receiver 626. A bore in the center of the post serves as the passage. Light source 618 may be mounted on circuit board 619 within capsule housing 610, where other circuits for the capsule camera may also be mounted on the board. Light receiver 626 may be mounted on PCB 628 where other circuits for the docking system can be implemented. The bore in the post is aligned with the longitudinal axis of the capsule device to allow light emitted from the light source 618 to pass through the light passage to reach light receiver 626. The capsule device is shown partially into the inner surface of the shell (i.e., primary core 624) so that the batteries remain outside the shell to reduce the influence of the magnetic flux on the batteries. A recessed structure (629) is formed in the center of the base part (620) of the docking device and is used as a receptacle for the capsule device.

The capsule retrieved after it exits from the anus may still have some remaining battery power, which may prevent the capsule circuits from resetting properly. In order to ensure proper data retrieval operation, an internal power off switch under the control of an external magnetic field is applied. Accordingly, magnet 632 is incorporated in holder/cover part 630. When the hold/cover is at a close position, the internal switch will be under the influence of the magnetic force to cause the batteries disconnected from the capsule circuits.

Figure 7:
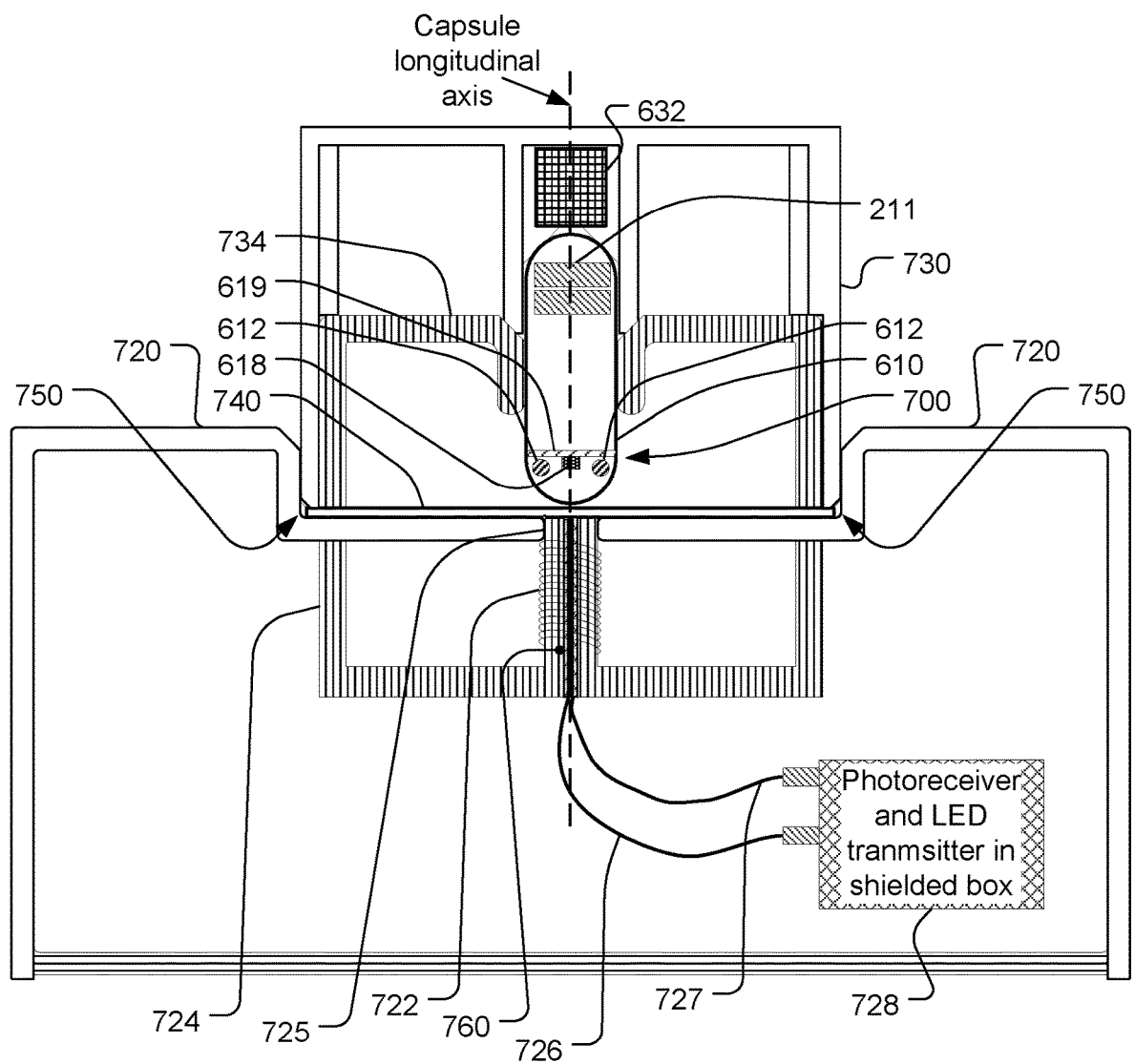
FIG. 7 illustrates a cross-section view of an exemplary optical wireless docking system according to the present invention, where the system is configured with longitudinal-field geometry and an uplink is provided using optic fibers as transmission media.

An alternative docking system according to the present invention is shown in FIG. 7, where optical communication link, named uplink, from the docking system to the capsule is also provided. The uplink allows the system to provide commands, controls, acknowledgements, programming or testing to the capsule. The data speed for the uplink does not have a high speed requirement. In order to provide the uplink, one or more light receiving devices (not shown in FIG. 7), such as photoresistors, phototransistors and photodiodes are used inside the capsule camera. Since the center location has been used by the light source in the capsule, the light receiving device(s) will be arranged off center inside the capsule.

The docking system consists of base part 720 and holder part or cover part 730. Holder/cover part 730 can be pulled open or separated from the base part to insert or remove capsule 700. The capsule camera illustrated is substantially the same as capsule camera 600 in FIG. 6. The parts that are the same are assigned the same numerical references. Primary coil 722 is wrapped around center post 725 of primary ferrite 724. The primary ferrite structure provides a passage to allow two optic fibers running between light source 618 and a light receiver (not shown) inside capsule housing 610 and light receiver/light transmitter 728 respectively. While light receiver/light transmitter 728 is shown as a standalone box, receiver/light transmitter 728 may also be mounted on a circuit board, where the same board also includes other circuits for the docking unit. An additional ferrite (734) is shown in holder/cover part 730 in FIG. 7, where the additional ferrite can be configured to direct more magnetic fluxes to go through the secondary coil. Primary core 724 in the base part of the docking device and the additional ferrite (734) in the holder/cover form a shell to provide needed shielding of the magnetic flux.

The two-way communication can be operated in half duplex or full duplex. The communication may adopt spatial or wavelength division multiplexing to avoid cross talk. A transparent window between capsule 600 and tips of light pipes 726 and 727 to allow optical signals passed between capsule 700 and light receiver/light transmitter 728. Again, the bore in the center of the post serves as the passage. The bore in the post is aligned with the longitudinal axis of the capsule device as shown in FIG. 7. The light pipes can be optical fibers. Accordingly, transparent piece 740 is placed on the concaved top side of base part 720. The capsule may not be fully cleaned and dried when it is inserted into the docking station. To prevent any liquid to leak into the base part, it is desirable to seal between the edges of transparent piece 740 and base part 720 as indicated by arrows 750. Ferrule 760 may be used to strengthen optical fibers 726 and 727 and keep them in position.

Figure 8:
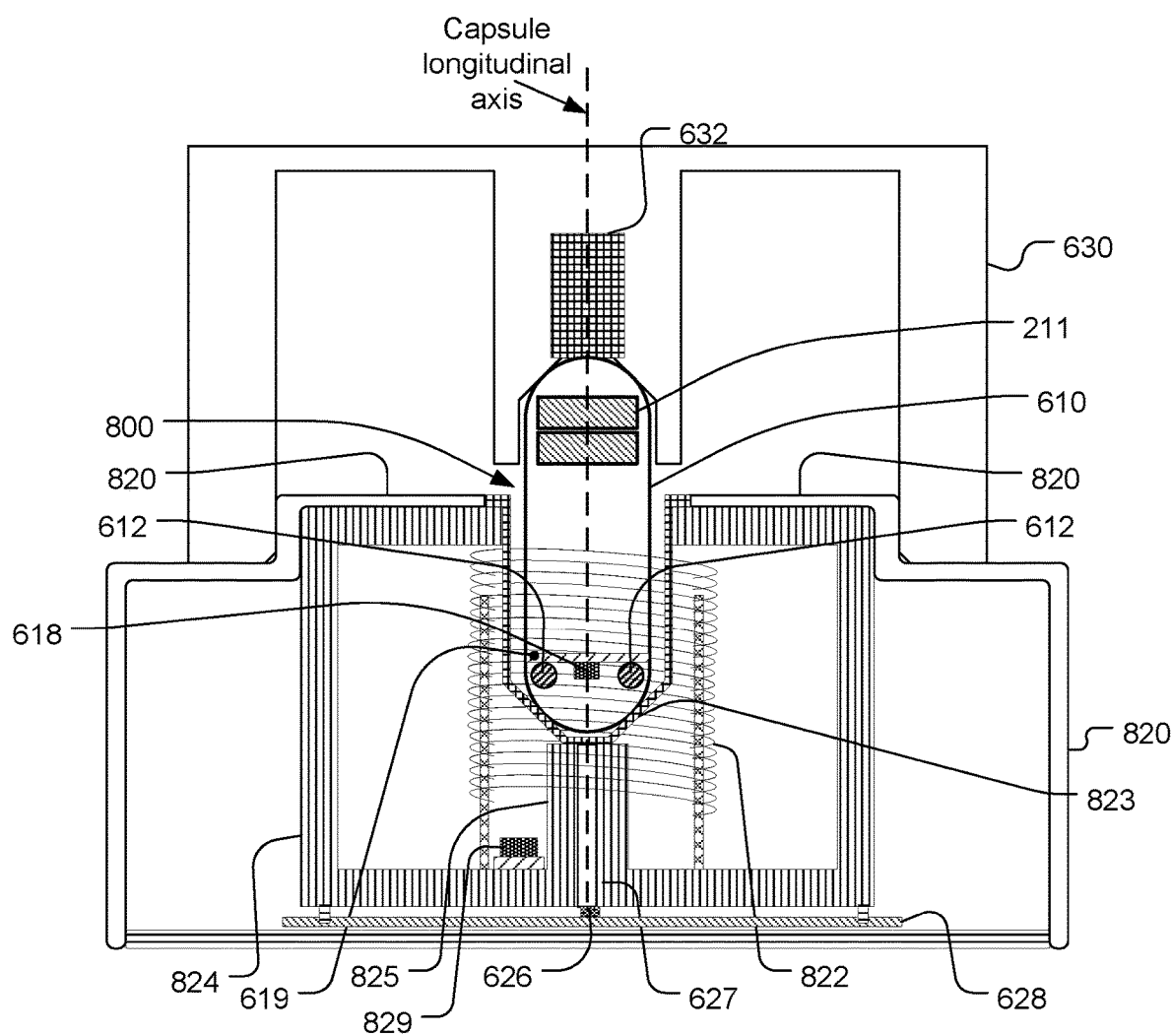
FIG. 8 illustrates a cross-section view of another exemplary optical wireless docking system according to the present invention, where the system is configured with longitudinal-field geometry and an uplink is provided using space as transmission media.

Yet another alternative docking system according to the present invention is shown in FIG. 8, where an uplink is also provided. Unlike the docking system in FIG. 7 where optic fibers are used as a transmission media, the docking system in FIG. 8 uses space as transmission media. For the uplink, LED transmitter 829 is used as a light source and one or more photoresistors inside the capsule housing (not shown in FIG. 8) are used as light receivers. Since the center location has been used by the light source in the capsule, the light receiving device(s) will be arranged off center inside the capsule. The docking system consists of base part 820 and holder part or cover part 630, which are substantially the same as these in FIG. 6. Also, capsule camera 800 illustrated is similar to the capsule camera 600 of FIG. 6. However, an optical receiver is incorporated in the capsule device to receive the uplink signal emitted from the optical transmitter in the docking device. The parts that are the same are assigned the same numerical references. The base part 820 includes ferrite primary core 824 and center post 825. The space between primary coil 822 and center post 825 is used to accommodate LED transmitter 829.

Capsule 800 may include one or more photoresistors inside the capsule housing to be used as optical receiver for receiving light from LED 829. The two-way communication can be operated in half duplex or full duplex. The communication may adopt spatial or wavelength division multiplexing to avoid cross talk. FIG. 8 also illustrates a different design for the receptacle (823), where the receptacle comprises a tapered inner surface to mate with the curved surface of one longitudinal end of the capsule device to align a longitudinal axis of the capsule device with the optical receiver in the docking device. At least a portion of the receptacle is transparent to allow light to pass through the capsule device. A bore in the center of the post serves as the passage. The bore in the post is aligned with the longitudinal axis of the capsule device to allow light emitted from the light source 618 to pass through the light passage to reach light receiver 626.

Figure 9:
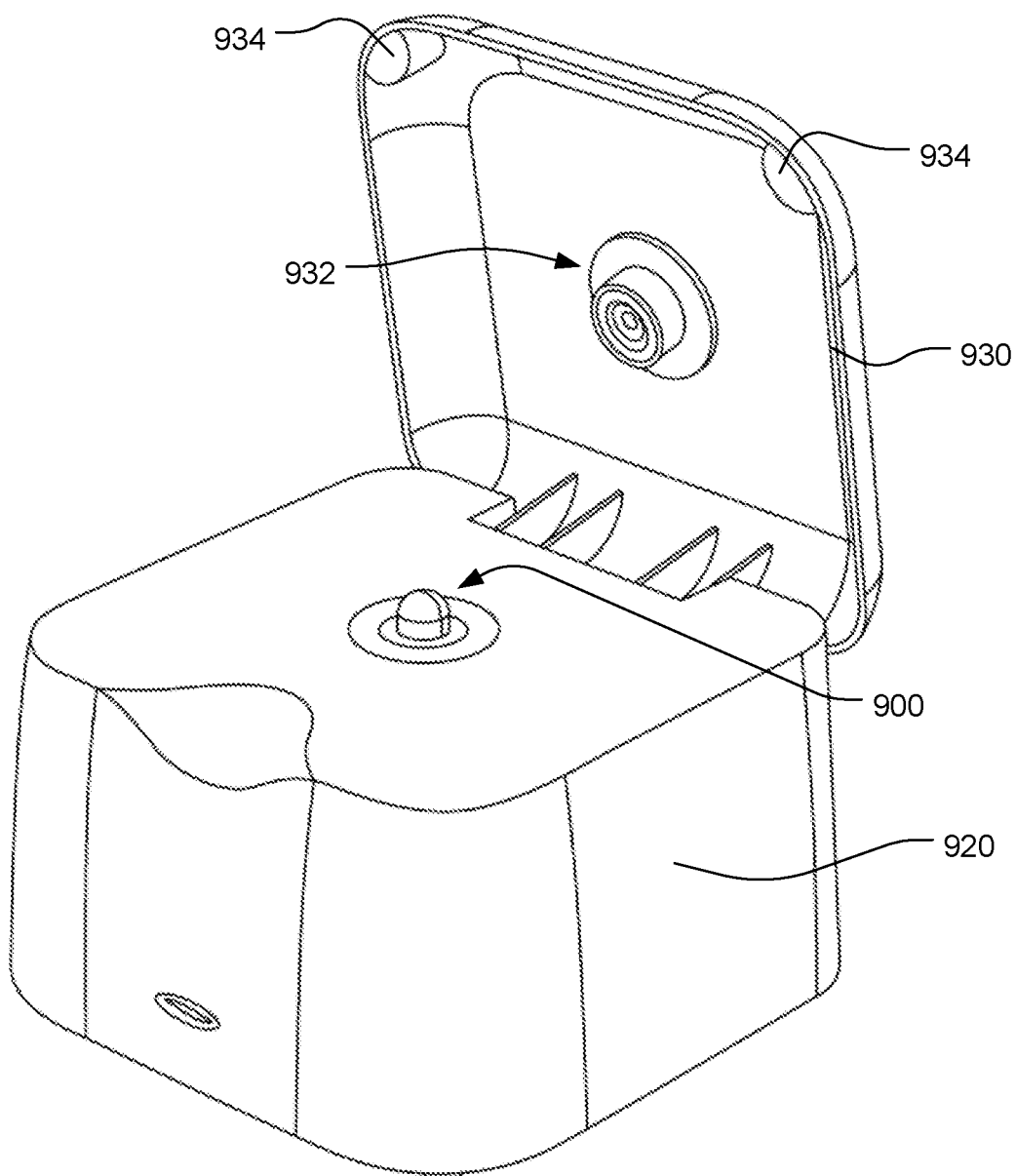
FIG. 9 illustrates an exemplary optical wireless docking system according to the present invention.
Figure 10:
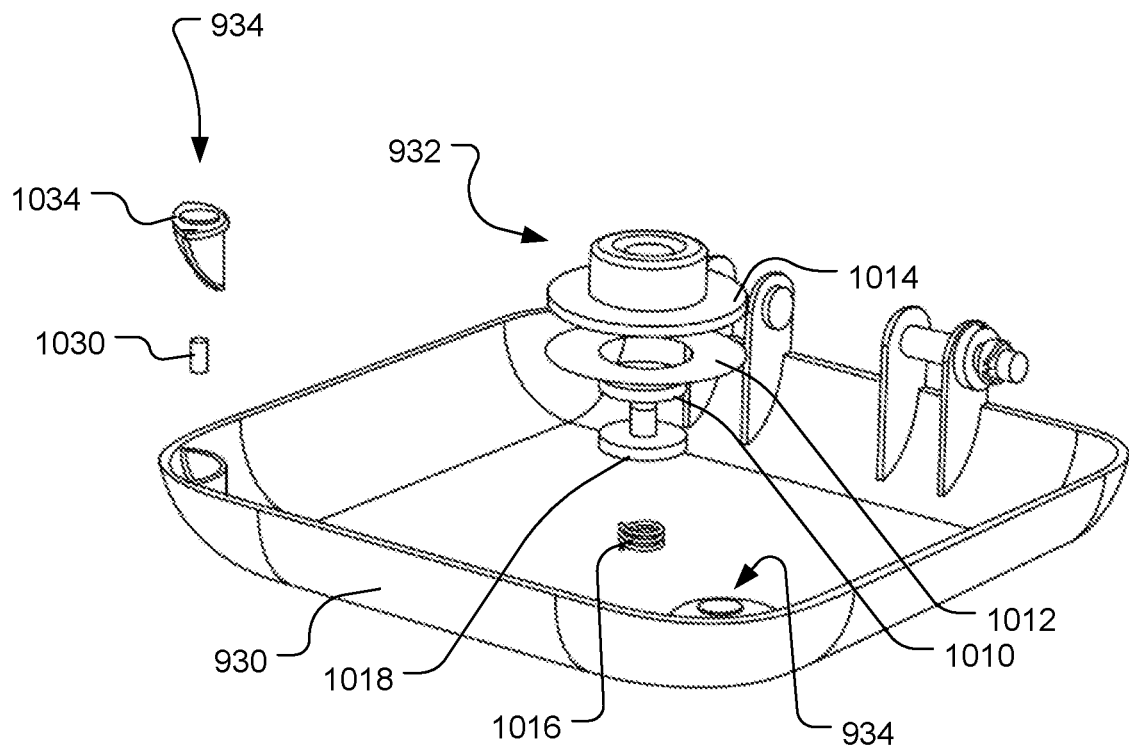
FIG. 10 illustrates an exploded view of the hinged lid of the optical wireless docking system in FIG. 9.

FIG. 9 illustrates a docking system embodying the present invention. The docking system comprises lid/cover part 930 and base part 920. Capsule 900 is situated in the capsule bay of the base part. The cover includes sub-assembly 932 and subassembly 934. FIG. 10 illustrates more detailed structure of lid/cover part 930, where the lid/cover part is shown upside down. An exploded view of subassembly 932 and subassembly 934 is shown. Subassembly 932 comprises magnet 1010, VHB (adhesive) 1012, flange 1014, compression spring 1016, and plunger 1018. The subassembly 934 comprises magnet 1030 and bumper 1032. When lid/cover 930 is lowered to a closed position, magnet 1010 will be a short distance from capsule 900. The magnetic force of magnet 1010 will cause capsule 900 to disconnect at least some of its circuits from the batteries. Plunger 1018 is spring-loaded. When the lid/cover part is opened, the plunger will push capsule 900 away from magnet so that it is pushed to the bottom of the "bay" (receptacle) and does not lift. Bumper 1032 can absorb some impact force when the lid is closed down and magnet 1030 can interact with a second magnet, a ferromagnetic component, or a ferrimagnetic component in the base part to provide a holding force between the lid and the base part.

Figure 11:
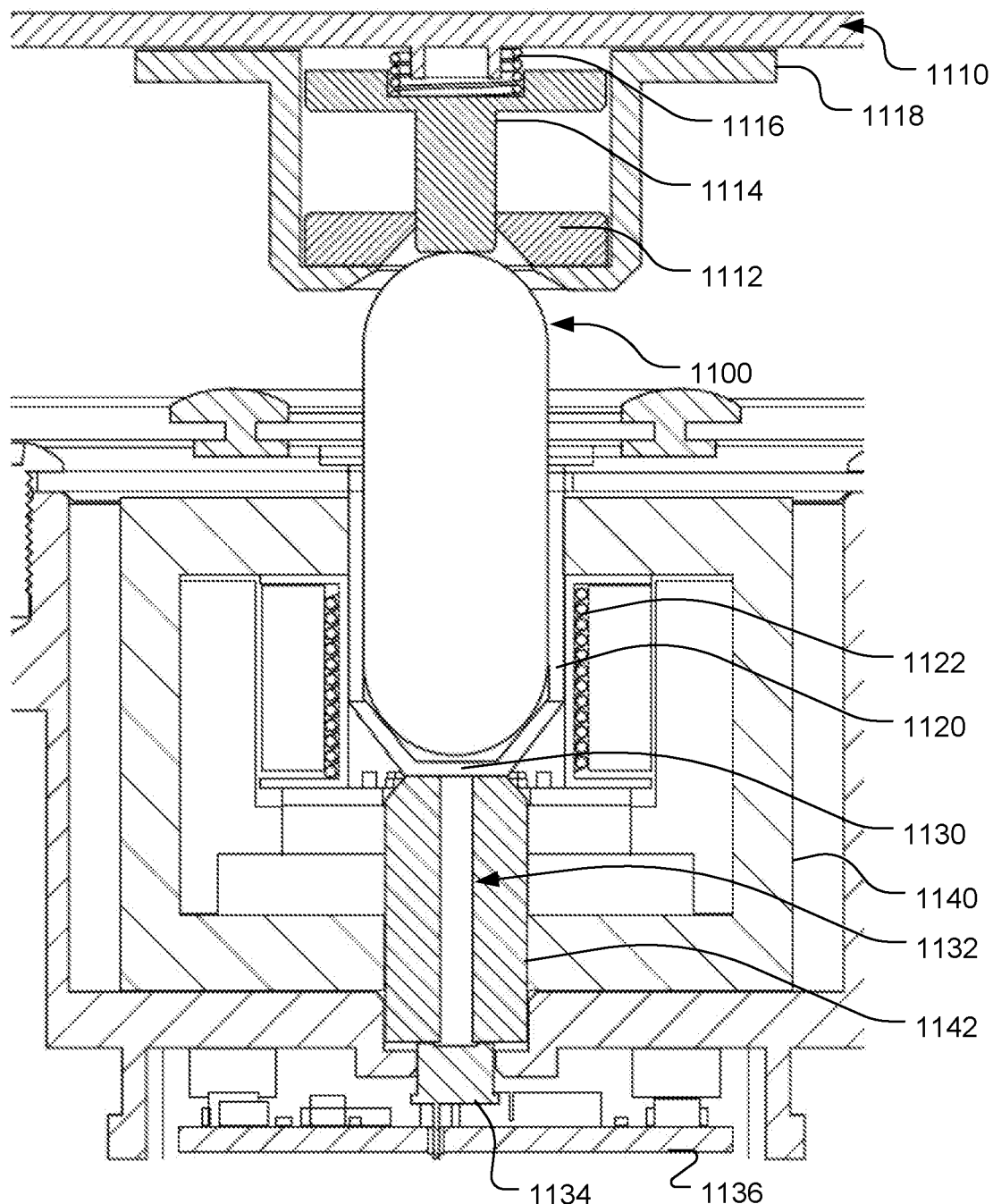
FIG. 11 illustrates a cross-section view of the exemplary optical wireless docking system in FIG. 9.

A portion of a cross section drawing of a capsule docking station incorporating an embodiment of the present invention is shown in FIG. 11. Capsule 1100 sits in receptacle 1120. A ring-shaped magnet (1112) with a tapered bore is held in hinged lid 1110 and comes into close proximity of the capsule when the lid is lowered. A compression spring (1116) along with plunger 1114 and magnet 1112 are housed in retention cap 1118. When the lid is in a closed position, the plunger pushes the capsule down toward the bottom of the receptacle. The lower portion of FIG. 11 corresponds to the cross section of the base part of the docking device. The receptacle in the base part is used to receive the capsule. The bottom of the receptacle corresponds to a transparent window (1130) to allow light to pass between the capsule and light receiver 1134 through passage 1132, which may contain an optical fiber or light pipe. The taper in the sides of receptacle 1120 near the bottom centers the capsule with the passage 1132. The light receiver can be mounted on PCB 1136. Also shown in FIG. 11 are ferrite 1140, ferrite post 1142 and primary coil 1122. The secondary coil inside the capsule is not shown in FIG. 11. The magnet must come to within about 0.2 mm of touching the capsule to reliably disconnect the batteries from electrical circuits in the capsule.

When the capsule is attracted to the magnet, the optical coupling will be reduced if it lifts up off the bottom of the receptacle to meet the magnet. The capsule must rest on the taper of the receptacle to be properly aligned to the optical fiber. Also, when the lid is lifted, it will take the capsule with it. In order to overcome these problems, the system includes a spring-loaded plunger that passes through the bore of the magnet. The plunger pushes the capsule down into the receptacle during download and also as the lid is lifted, until the plunger is fully extended. Without a holding force, the lid would be pushed up by the plunger spring. It must be held down somehow during download. Accordingly, the lid has two lid magnets that are attracted to magnets in the base and these magnets hold the lid down. These lid magnets should not be so strong that the entire system is lifted up off the table when the lid is lifted.

Figure 12:
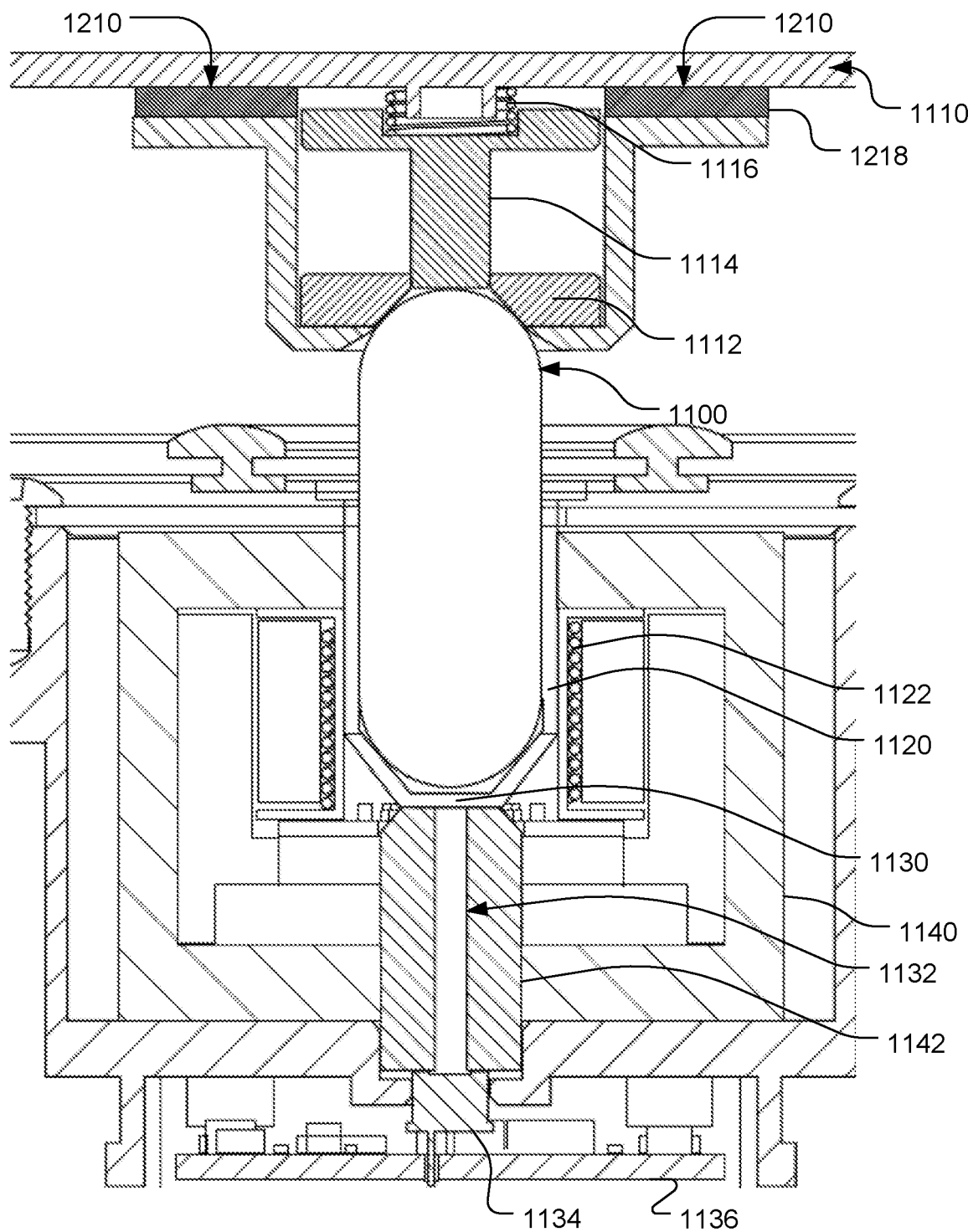
FIG. 12 illustrates a cross-section view of an optical wireless docking system, where foam is added between the lid and the retention cap.

One embodiment according to the present invention is to introduce compliance into the plunger magnet position with the addition of a spring connecting the magnet to the lid. The compliance compensates for mechanical tolerances so that the magnet will reliably touch the capsule or sit sufficiently close to the capsule (e.g. less than 0.2 mm) to cause the capsule to disconnect internal circuits from the batteries while the lid is closed and the capsule is pushed to the bottom of the receptacle. Adhesive-backed foam 1210 is inserted between the retention cap (1218) and the lid as shown in FIG. 12. The foam is a form of spring that provides some compliance to the magnet position.

Figure 13:
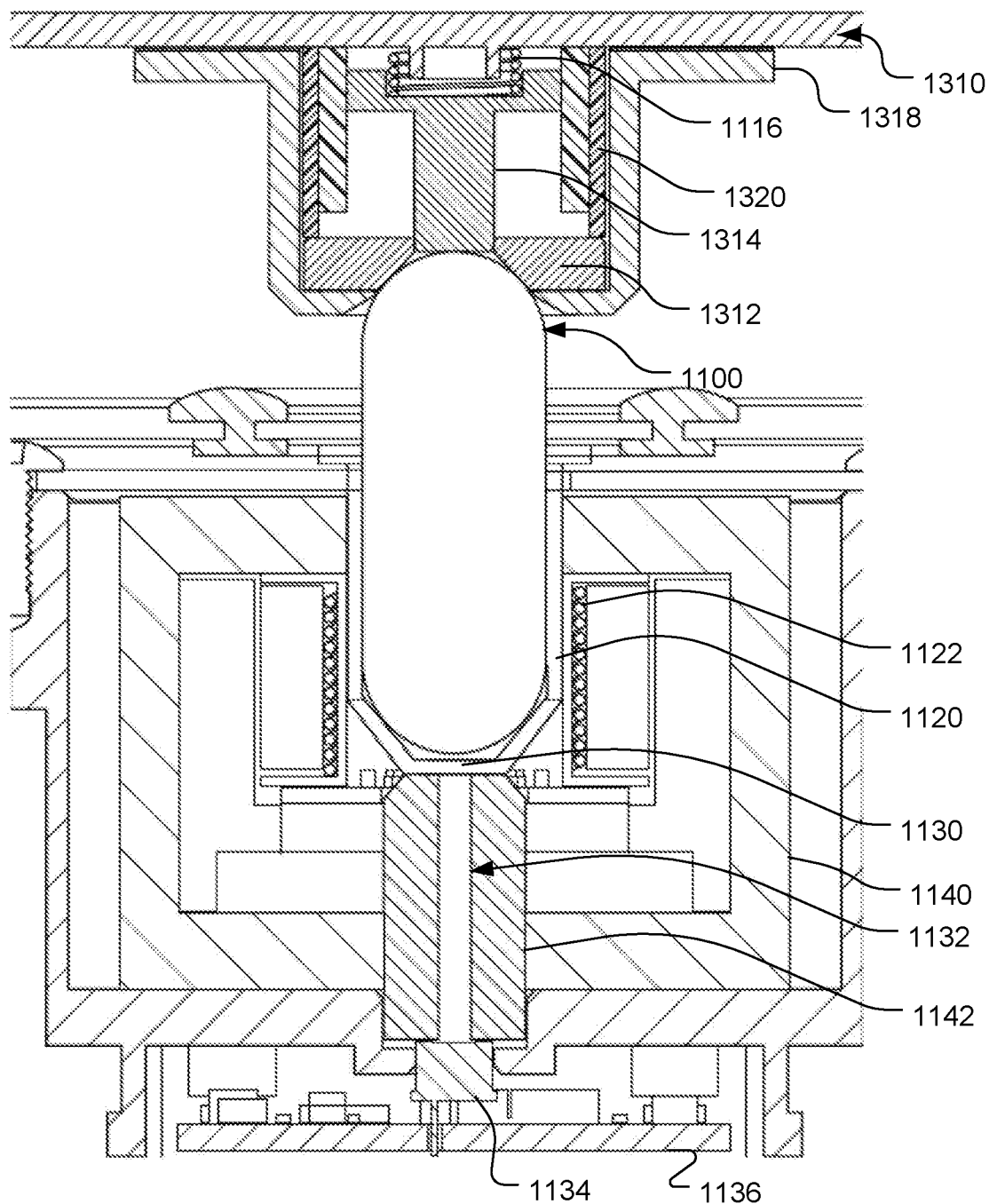
FIG. 13 illustrates a cross-section view of an optical wireless docking system, where a push force is applied to the capsule device by a spring when the lid is opened.

One embodiment according to the present invention is shown in FIG. 13. Instead of gluing the magnet to the retention cap, a spring (1320) loaded with a short range of vertical travel is used to provide compliance to the magnet. The flange on plunger 1314 is reduced in diameter to fit inside an inner cylinder. The spring pushing magnet 1312 sits between the inner cylinder and retention cap 1318. The spring force needs only be strong enough to keep the plunger pushed against the capsule and prevent rattling when lid 1310 is moved.

There is a potential problem with the designs shown above. The liquids remaining on the capsule can flow into the retention cap through the gap between the plunger and the plunger magnet. If the magnet is movable, then another gap exists around the outside of the magnet. The capsule will touch the plunger and the magnet. If the capsule is still wet, this moisture could wick into the opening, become trapped, and lead to microbial growth. Also, users may want to wipe down and disinfect the system. Cleaning liquids could also flow through the opening and become trapped. A design that seals this region may be desirable.

Figure 14:
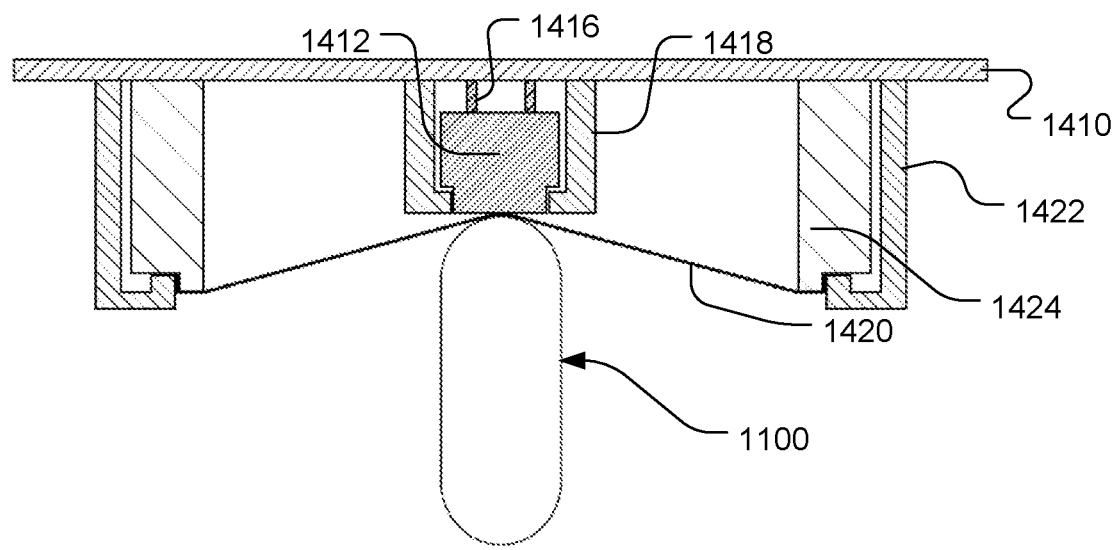
FIG. 14 illustrates a cross-section view of an optical wireless docking system, where an elastic membrane is used to provide water tight feature and push force on the capsule device when the lid is opened.

Accordingly, one embodiment of the present invention to achieve a liquid barrier is shown in FIG. 14. The ring magnet is replaced by a rod magnet (1412). The rod magnet has the advantage of relaxing the lateral alignment requirement between the capsule receptacle and the magnet on the lid (1410). The magnet has a short travel distance which takes up all of the vertical tolerance stack-up. The magnet is pushed downward by a soft spring (1416), whose main function is to prevent the magnet rattling around in its bore. A flexible membrane (1420) covers the magnet assembly (1418) and provides a seal. In FIG. 14, membrane 1420 is elastic and acts like a trampoline to provide the force F_Plunger pushing the capsule down. The membrane needs to be a material that retains its mechanical properties after exposure to the environment, including modest levels of UV light and alcohol and other mild cleaning agents. Also, the membrane should be tough enough to resist puncture and abrasion under reasonable use. Polyester polyurethane can meet these requirements. The membrane can be made taught by gluing it to an outer ring (1422) and then pressing it over a step (1424) as shown in FIG. 14.

Figure 15:
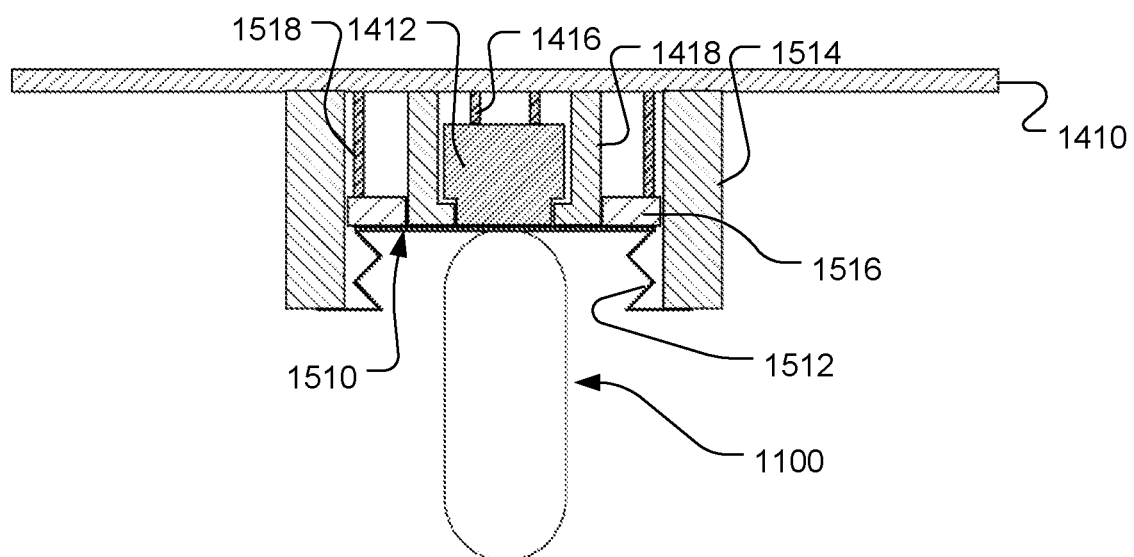
FIG. 15 illustrates a cross-section view of an alternative optical wireless docking system with an elastic membrane to provide water tight feature and push force on the capsule device when the lid is opened.

Another embodiment of the present invention to achieve a liquid barrier is shown in FIG. 15, where the membrane (1510) is inelastic and is bonded to a ring (1516). The force F_Plunger pushing on the capsule is provided by a second spring (1518) pushing on ring 1516. An accordion (1512) or similar structure allows the membrane and ring to move without breaking the seal. Cap structure 1514 is attached to the lid to provide travel space for ring 1516 and also allow the accordion structure to be affixed to cap structure 1514. While exemplary arrangements to achieve a liquid barrier are shown in FIG. 14 and FIG. 15, a person skill in the art may use other similar arrangement to achieve a liquid barrier.

Instead of a plunger or elastic membrane providing a force F_Plunger pushing the capsule away from the magnet, a frictional force may be employed to hold the capsule in the receptacle when the lid is lifted. The frictional force must exceed the force of the magnet. The frictional force may be supplied by compliant member that presses against the side of the capsule. The receptacle might be flexible, in which case the user must push the capsule into the receptacle and some force is required to overcome the frictional holding force and pull it out. Alternatively, the rubber ring mating the receptacle to the housing in FIG. 11 may have a reduced inner diameter so that it interferes with the capsule, bends when the capsule is inserted, and applies a holding force. A clamp may also be used to hold the capsule in the receptacle while the lid is lifted. The clamp may engage automatically or be actuated by the user.

Instead of preventing the capsule from being pulled out of the receptacle when the lid is lifted, the system may have the feature that the capsule is removed from the receptacle when the lid is lifted, held by the magnet. The user may then remove the capsule from the magnet. The system should be designed to either repeatably lift the capsule with the lid or repeatably leave the capsule in the receptacle when the lid is lifted so that the behavior is predictable to the user.

In another embodiment, the capsule may have a magnetically actuated switch located in another location internal to the capsule besides the capsule tip. Also, the switch may be sufficiently sensitive to a magnetic field such that a magnet may be positioned close to, but not touching the capsule. The magnet may be positioned in the base of the docking system on one or more sides of the capsule receptacle, rather than on the lid. For example, a longitudinal magnetic field could be produced in the capsule by one or more rod magnets with vertical polarity located on one or more sides of the capsule (when it is in the receptacle in the docking system) or a ring magnet could be positioned around the capsule. The switch might be actuated by a transverse field, in which case a magnet with lateral polarity could be positioned to the side of the capsule, and, in this case, the capsule rotational orientation might need to be aligned relative to the direction of the magnetic field. The magnetic field could be produced by a permanent magnet or an electromagnet.

The docking devices as shown in FIGS. 6-15 incorporate a lid and a magnet. The magnet will cause the capsule to disconnect the batteries from electrical circuits inside the capsule when the lid is closed. In another embodiment of the present invention, the need for the magnet and lid is obviated. The capsule firmware periodically polls for a docking system signal so that the capsule does not require power-on reset prior to download. Therefore, there is no need to use a magnet to cause the capsule to disconnect the batteries from the electrical circuits inside the capsule.

Without the magnet and the lid, the docking system will have no moving parts. As such, it will be easier to ensure usability, reliability, and durability of the product. The lid hinge area is the most likely section to break if the system is dropped or otherwise abused. The assembly process will be simplified. Also, the cost associated with the docking device can be reduced.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A capsule endoscopic system comprising a docking device for receiving a capsule device, wherein the capsule device comprises:
    a battery;
    a secondary coil that conducts a current when an alternating magnetic field is present;
    an optical transmitter for transmitting an optical signal, the optical transmitter being coupled to the secondary coil to receive power derived from the current in the secondary coil; and
    a capsule housing that encloses the battery, the secondary coil, and the optical transmitter in a sealed environment, the sealed environment having a first portion and a second portion that are separated from each other, wherein the battery is provided in the first portion, and wherein the secondary coil is provided in the second portion;
and a docking device, wherein the docking device comprises:
    a base enclosure having a receptacle for holding the capsule device in a docked position;
    a primary coil for generating the alternating magnetic field;
    a primary core configured for concentrating the alternating magnetic field in the vicinity of the second portion of the sealed environment, as positioned by the receptacle when the capsule device is held in the docked position, such that the second portion of the sealed environment receives a greater magnetic flux from the concentrated alternating magnetic field than the first portion of the sealed environment; and
    an optical receiver to receive the optical signal from an optical path situated between the optical transmitter, as positioned by the receptacle when the capsule device is held in the docked position, and the optical receiver.

2. The capsule endoscopic system of claim 1, wherein the optical path is collinear with a longitudinal axis of the capsule device.

3. The capsule endoscopic system of claim 2, wherein the receptacle positions the capsule housing such that the longitudinal axis of the capsule device is stationary as the capsule device is rotated in the docked position.

4. The capsule endoscopic system of claim 1, wherein the primary core includes a post that has an axis substantially parallel to the optical path.

5. The capsule endoscopic system of claim 4, wherein the post has a bore through the axis of the post, and wherein the optical path passes through the bore.

6. The capsule endoscopic system of claim 5, wherein the receptacle comprises a tapered inner surface to mate with a curved surface of a first longitudinal end of the capsule device, such that the optical path passes through the first longitudinal end of the capsule device.

7. The capsule endoscopic system of claim 6, wherein at least a portion of the first longitudinal end of the capsule device is transparent to allow light from the optical transmitter to pass through.

8. The capsule endoscopic system of claim 1, wherein the capsule device further comprises an archival memory to store data captured when the capsule device traveled through a human GI (gastrointestinal) tract, and the archival memory is enclosed in the capsule housing.

9. The capsule endoscopic system of claim 8, wherein the capsule device further comprises a control circuit coupled to the archival memory and the optical transmitter, and wherein the control circuit is configured to read stored data from the archival memory and to provide the stored data to the optical transmitter.

10. The capsule endoscopic system of claim 1, wherein the optical transmitter generates modulated light.

11. The capsule endoscopic system of claim 10, wherein the docking device comprises a lens of positive refractive power to reduce divergence of the modulated light.

12. The capsule endoscopic system of claim 1, wherein the receptacle comprises a tapered inner surface to mate with a curved surface of a first longitudinal end of the capsule device, and wherein the optical path passes through to the first longitudinal end of the capsule device.

13. The capsule endoscopic system of claim 12, wherein at least a portion of the first longitudinal end of the capsule device is transparent to allow light from the optical transmitter to pass through.

* * * * *